United States Patent [19]
Favre et al.

[11] Patent Number: 6,123,960
[45] Date of Patent: Sep. 26, 2000

[54] COMPOSITION BASED ON LIPID VESICLES AND A CROSS-LINKED POLY(2-ACRYLAMIDO-2-METHYLPROPANE-SULPHONIC ACID) WHICH IS AT LEAST 90% NEUTRALIZED

[75] Inventors: Sophie Favre, Chevilly Larue; Nadia Terren, Bourg La Reine, both of France

[73] Assignee: L'Oreal, Paris, France

[21] Appl. No.: 09/110,445

[22] Filed: Jul. 7, 1998

[30] Foreign Application Priority Data

Jul. 8, 1997 [FR] France ................... 97 08673

[51] Int. Cl.$^7$ ..................... A61K 9/127
[52] U.S. Cl. ............ 424/450; 424/401; 514/844; 428/402.2
[58] Field of Search ............ 424/450, 401, 424/1.21, 9.321, 9.51, 417, 94.3; 514/844; 428/402.2; 935/54

[56] References Cited

U.S. PATENT DOCUMENTS 5,368,850  11/1994  Cauwet et al. .
5,531,993  7/1996   Griat .

FOREIGN PATENT DOCUMENTS

| 0 642 781 | 3/1995 | European Pat. Off. . |
| 0 728 459 A1 | 8/1996 | European Pat. Off. . |
| 0 728 459 B1 | 3/1997 | European Pat. Off. . |
| 2 698 004 | 5/1994 | France . |
| 2 709 666 | 3/1995 | France . |
| 2 725 369 | 4/1996 | France . |

OTHER PUBLICATIONS

Kazuhiko Ishihara et al., "Specific Interaction between Water–Soluble Phospholipid Polymer and Liposome", Journal of Polymer Science, Part A, vol. 29, 1991, pp. 831–835.

English Language Derwent Abstract of EP 0 728 459 A1 and EP 0 728 459 B1.

English Language Derwent Abstract of FR 2 709 666.

English Language Derwent Abstract of FR 2 725 369.

*Primary Examiner*—Gollamudi S. Kishore
*Attorney, Agent, or Firm*—Finnegan, Henderson, Farabow, Garrett & Dunner, L.L.P.

[57] ABSTRACT

A cosmetic and/or dermatological composition comprising an aqueous dispersion of lipid vesicles containing at least one cross-linked poly(2-acrylamido-2-methylpropanesulphonic acid) polymer which is at least 90% neutralized, comprising, distributed in a random manner:

a) from 90 to 99.9% by weight of units of formula (1):

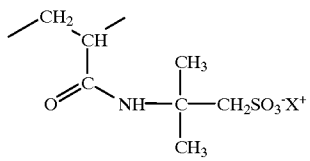

(1)

in which $X^+$ denotes at least one cation wherein no more than 10 mol % of the cations $X^+$ are protons $H^+$;

b) from 0.01 to 10% by weight of cross-linking units obtained from at least one monomer having at least two olefinic double bonds;

wherein the percentages by weight are relative to the total weight of the polymer.

49 Claims, No Drawings

COMPOSITION BASED ON LIPID VESICLES AND A CROSS-LINKED POLY(2-ACRYLAMIDO-2-METHYLPROPANE-SULPHONIC ACID) WHICH IS AT LEAST 90% NEUTRALIZED

The present invention relates to a composition comprising an aqueous dispersion of lipid vesicles and a cross-linked poly(2-acrylamido-2-methylpropanesulphonic acid) polymer which is at least 90% neutralized. It also relates to its uses in topical application.

Cosmetically or dermatologically active acid compounds such as hydroxy acids, α- and β-keto acids are increasingly used in the cosmetic field for facial and/or body care. In particular, hydroxy acids are used more especially to give the face a radiant and bright complexion and therefore a good, smooth and younger appearances, for the cosmetic treatment of wrinkles and/or of fine lines on the skin as well as to remove comedones caused by acne.

The compositions conventionally used in the cosmetic and/or dermatological fields are water-in-oil (W/O) emulsions, oil-in-water (O/W) emulsions or aqueous gels, into which it is often difficult or even impossible to incorporate organic acidic active agents such as kojic acid, caffeic acid, salicylic acid and its derivatives.

In general, these acidic active agents have a tendency to recrystallize or to become degraded. This results in a greater or lesser loss of efficacy of these compositions depending on the degree of recrystallization and/or of degradation, which runs counter to the desired objective. In addition, this recrystallization or degradation can modify the overall stability of these compositions as well as their appearance, which can put the user off these compositions affording specific treatment.

To solubilize some of these active agents, it is known to use W/O or O/W emulsions in which the aqueous phase has an acidic pH. For these emulsions to be stable (non-separation of the aqueous and oily phases), it is necessary to use emulsifiers (or surfactants). Unfortunately, these surfactants are often irritating to the skin. In addition, these emulsions often lack freshness upon application, which can hamper their uses during the hot periods of the year and/or in hot countries. An aqueous gel is a lot more appreciated under these conditions of use. However, its excessively large quantity of water does not allow the introduction therein of active agents exhibiting a degree of lipophilic character. The stability of these gels is moreover poor.

The need therefore remains for a stable composition which can be used in the cosmetic and/or dermatological fields, allowing sufficient solubilization of the acidic active agents generally used in these fields for a maximum efficacy. Moreover, a sufficiently high viscosity is also sought in the cosmetic field in order to facilitate the taking of the product out of its packaging without significant loss, limit the diffusion of the product to the local area of treatment and to be able to use it in sufficient quantities in order to obtain the desired cosmetic or dermatological effect. This objective is important for formulations such as those of care, hygiene or make-up products which have to be spread homogeneously over the local surface to be treated. To satisfy these conditions, the viscosity of the compositions is generally increased by adding thickening and/or gelling polymers.

There are known in European Patent Application EP-A-0,728,459 stable acidic formulations comprising this type of active agent, in the form of an oil-in-water dispersion comprising lipid vesicles acting as dispersant for the oil in the aqueous continuous phase. These formulations exhibit qualities in terms of application, make-up application and comfort which are specific to the formulations having vesicular systems as base. To obtain a satisfactory consistency for a comfortable application and an effective activity, conventional water-soluble gelling polymers such as cellulose derivatives, natural gums and synthetic polymers such as CARBOPOL and more particularly the mixture of polyacrylamide, isoparaffin and oxyethylenated lauryl alcohol containing 7 moles of ethylene oxide, sold under the name SEPIGEL 305 by the company SEPPIC are generally incorporated into these formulations.

The CARBOPOL-type thickening agents are generally incompatible with the acidic active agents and do not lead to the desired consistency. Natural gums such as cellulose gums or xanthan gums most often lead to gummy or even sticky formulations.

The mixture of polyacrylamide, isoparaffin and oxyethylenated lauryl alcohol containing 7 moles of ethylene oxide, sold under the name SEPIGEL 305 by the company SEPPIC, has the disadvantage of containing surfactants which have an irritant potential towards the skin. Furthermore, the vesicular formulations containing this thickening agent have a tendency, at the end of the application to the skin, to give a slightly sticky feel.

The inventors have surprisingly discovered a new family of surfactant-free gelling polymers which make it possible to obtain cosmetic and dermatological formulations based on lipid vesicles in the form of stable and homogeneous oil-in-water dispersions which make it possible to resolve the abovementioned disadvantages and in particular to solubilize and stabilize the acidic organic active agents at pH values of less than or equal to 5. Moreover, the dispersions obtained according to the invention are unexpectedly substantially finer than those of the prior art and are easier and more comfortable to spread on the skin.

Accordingly, the subject of the invention is a cosmetic and/or dermatological composition containing an aqueous dispersion of lipid vesicles and at least one cross-linked poly(2-acrylamido-2-methylpropanesulphonic acid) which is at least 90% neutralized.

Another subject of the invention is a cosmetic and/or dermatological composition containing an aqueous dispersion of lipid vesicles, characterized in that it contains at least one acidic compound conferring an acidic pH on the dispersion and at least one cross-linked poly(2-acrylamido-2-methylpropanesulphonic acid) which is at least 90% neutralized.

The cross-linked poly(2-acrylamido-2-methylpropanesulphonic acid) polymers which are practically or completely neutralized, in accordance with the invention, are water-soluble or are capable of swelling in water. They are in general characterized in that they comprise, distributed in a random manner:

a) from 90 to 99.9% by weight of units of the following general formula (1):

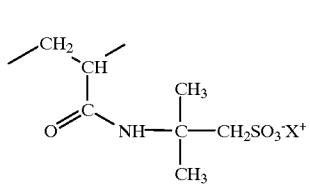

in which $X^+$ denotes at least one cation, it being possible for at most 10 mol % of the cations $X^+$ to be protons $H^+$;

b) from 0.01 to 10% by weight of cross-linking units obtained from at least one monomer having at least two olefinic double bonds; the proportions by weight being defined relative to the total weight of the polymer.

Thus, the polymers of the invention are homopolymers, that is to say polymers obtained through the polymerisation of a monomer, said monomer being in the present invention the units of formula (1).

Preferably, the polymers of the invention comprise a number of units of formula (1) in a sufficiently large quantity to obtain a hydrodynamic volume of the polymer in a solution of water having a radius ranging from 10 to 500 nm, of homogeneous and unimodal distribution.

The polymers according to the invention which are more particularly preferred comprise from 98 to 99.5% by weight of units of formula (1) and from 0.2 to 2% by weight of cross-linking units.

$X^+$ represents a cation or a mixture of cations preferably selected from a proton, an alkali metal cation, a cation equivalent to that of an alkaline-earth metal or the ammonium ion.

More particularly, 90 to 100 mol % of the cations are $NH_4^+$ cations and 0 to 10 mol % are protons ($H^+$).

The cross-linking monomers having at least two olefinic double bonds are selected, for example, from dipropylene glycol diallyl ether, polyglycol diallyl ethlers, triethylene glycol divinyl ether, hydroquinone diallyl ether, tetraallyl oxethanoyl or other polyfunctional allyl or vinyl ether alcohols, tetraethylene glycol diacrylate, triallylamine, trimethylolpropane diallyl ether, methylenebisacrylamide or divinylbenzene.

The cross-linking monomers having at least two olefinic double bonds are more preferably selected from those corresponding to the following general formula (2):

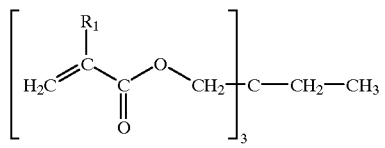

(2)

in which $R_1$ denotes a hydrogen atom or a $C_1$–$C_4$ alkyl and still more preferably methyl (trimethylolpropane triacrylate).

The reaction for polymerization of the polymers of the invention produces not only linear chains but also branched or cross-linked molecules of polymer. These molecules may be characterized in particular by their rheological behaviour in water, but more particularly by the dynamic scattering of light.

In the case of the characterization of the molecules by the dynamic scattering of light, the distribution of the hydrodynamic volume of the structures of the polymer is measured. The macromolecules dissolved in water are flexible and are surrounded by a salvation envelope consisting of water molecules. With charged polymers such as those of the invention, the size of the molecules depends on the quantity of salt in the water. In polar solvents, the uniform charge along the principal chain of the polymer leads to a substantial expansion of the polymeric chain. Increasing the quantity of salt increases the quantity of electrolyte in the solvent and shields the uniform charges on the polymer. In addition to the molecules transported into the solvation envelope, the solvent molecules are attached inside the cavities of the polymer. In this case, the solvent molecules are part of the macromolecules in solution and move at the same average speed. Thus, the hydrodynamic volume describes the linear dimension of the macromolecule and of these solvation molecules.

The hydrodynamic volume vh is determined by the following formula:

$$v_h = M/N_A \times (V_2 + dV_1)$$

with:
M denoting the mass, in grams, of the undissolved macromolecule;
$N_A$ denoting Avogadro's number;
$V_1$ denoting the specific volume of the solvent;
$V_2$ denoting the specific volume of the macromolecule;
d the mass, in grams, of the solvent which is associated with 1 gram of undissolved macromolecule.

If the hydrodynamic particle is spherical, it is then calculated from the hydrodynamic volume, the hydrodynamic radius by the formula:

$$V_h = 4 \prod R^3 / 3$$

with R denoting the dynamic radius.

Instances where the hydrodynamic particles are perfect spheres are extremely rare. The majority of synthetic polymers involve compacted structures or ellipsoids of high eccentricity. In this case, the radius is determined on a sphere which is equivalent, from a frictional point of view, to the shape of the particle considered.

As a general rule, the operations are carried out on molecular weight distributions and therefore on radius and hydrodynamic volume distributions. For the polydispersed systems, the distribution of the diffusion coefficients has to be calculated. The results relating to the radial distribution and to the distribution of the hydrodynamic volumes are deduced from this distribution.

The hydrodynamic volumes of the polymers of the invention are in particular determined by dynamic light scattering from the diffusion coefficients D according to STOKES-EINSTEIN of formula: $D=kT/6\Pi\eta R$ where k is the Boltzmann constant, T the absolute temperature in degrees Kelvin, $\eta$ is the viscosity of the solvent (water) and R is the hydrodynamic radius.

These diffusion coefficients D are measured according to the method of characterization of a mixture of polymers by LASER scattering described in the following references:

(1) Pecora, R; Dynamic Light Scattering; Plenium Press, New York, 1976;
(2) Chu, B; Dynamic Light Scattering; Academic Press, New York, 1994;
(3) Schmitz, K S; Introduction to Dynamic Light Scattering; Academic Press, New York, 1990;
(4) Provincher S. W.; Comp. Phys., 27, 213,1982;
(5) Provincher S. W.; Comp. Phys., 27, 229,1982;
(6) ALV Laservertriebgesellschaft mbH, Robert Bosch Str. 47, D-63225 Langel, Germany;
(7) ELS-Reimheimer Strasse 11, D-64846 Gross-Zimmern, Germany;
(8) CHI WU et al., Macromolecules, 1995, 28, 4914–4919, the disclosures of which are specifically incorporated herein by reference.

The polymers particularly preferred are those having a viscosity, measured in a BROOKFIELD viscometer in a solution of water at 2% and at 25° C., greater than or equal to 1000 cps and still more preferably ranging from 5000 to 40,000 cps and even more preferably from 6500 to 35,000 cps.

The cross-linked poly(2-acrylamido-2-methylpropanesulphonic acid) polymers of the invention can be obtained according to the method of preparation comprising the following steps:

(a) the 2-acrylamido-2-methylpropanesulphonic acid monomer is dispersed or dissolved in free form in a solution of tert-butanol or of water and tert-butanol;

(b) the solution or dispersion of AMPS monomer obtained in (a) is neutralized with one or more inorganic or organic bases, preferably aqueous ammonia $NH_3$, in a quantity which makes it possible to obtain a rate of neutralization of the sulphonic acid functional groups of the polymer ranging from 90 to 100%;

(c) the cross-linking monomer(s) is(are) added to the solution or dispersion obtained in (b);

(d) a conventional free-radical polymerization is carried out in the presence of initiators of free radicals at a temperature ranging from 10 to 150° C.; the polymer precipitating in the tert-butanol-based solution or dispersion.

The practically or completely neutralized, cross-linked poly(2-acrylamide-2-methylpropanesulphonic acid) polymers are present in the cosmetic or dermatological compositions of the invention in concentrations preferably ranging from 0.01 to 20% by weight relative to the total weight of the composition, and more preferably from 0.1 to 10% by weight.

The compositions in accordance with the invention are more particularly oil-in-water dispersions in which the lipid vesicles act as agent for dispersing oil in the aqueous continuous phase.

The lipid vesicles according to the invention can encapsulate an aqueous phase (aqueous core) or an oily phase (oily core). They are selected from those described and prepared in European Patent Application EP-A-0,728,459, the disclosure of which is specifically incorporated herein by reference.

The aqueous core-containing lipid vesicles in accordance with the invention are preferably vesicles comprising a lipid membrane obtained from nonionic amphiphilic lipids, ionic amphiphilic lipids or mixtures thereof.

The oily core-containing lipid vesicles in accordance with the invention are preferably oily globules in aqueous dispersion, coated with a monolamellar or an oligolamellar layer obtained from at least one lipophilic surfactant, one hydrophi is surfactant and either an ionic amphiphilic lipid or a fatty acid combined with a baisic agent dissolved in the aqueous phase of the dispersion. "Oligolamellar" layer is understood to mean a layer comprising from 2 to 5 lipid lamellae. These vesicles are described in French Patent Applications Nos. 94-12005 and 93-10588, the disclosures of which are specifically incorporated by reference herein. They are prepared according to a process involving mixing, in a first step, with stirring, the oily phase comprising the hydrophilic surfactant, the lipophilic surfactant, the ionic amphiphilic lipid or the fatty acid and the aqueous phase optionally containing the basic agent, and then in a second step, subjecting the mixture obtained to homogenization based on the principle of cavitation. This homogenization is obtained either using ultrasound, or using high pressures ranging from 200 to 1500 bar, or using homogenizers equipped with a rotor-stator head.

The amphiphilic nonionic lipids used for the preparation of the aqueous core-containing vesicles are preferably selected from:

1) linear or branched polyglycerol ethers of formula:

$$R^{10}O\text{---}[\text{---}C_3H_5\text{---}(OH)O\text{---}]_n\text{---}H \qquad (II)$$

in which:

—$C_3H_5(OH)O$ is represented by the following structures taken as a mixture or separately:

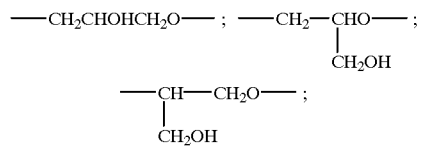

n is a mean statistical value ranging from 2 to 6;
$R^{10}$ represents:
  (a) a linear or branched aliphatic chain containing from 12 to 18 carbon atoms;
  (b) a residue $R^{11}CO$, where $R^{11}$ is a linear or branched, aliphatic $C_{11}$–$C_{17}$ radical;
  (c) a residue $R^{12}$—[—$OC_2H_3(R^{13})$—]—, where:
    $R^{12}$ may have the meaning (a) or (b) given for $R^{10}$;
    $OC_2H_3(R^{13})$— is represented by the following structures, taken as a mixture or separately:

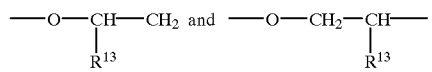

where $R^{13}$ has the meaning (a) given for $R^{10}$;

(2) polyoxyethylenated fatty alcohols, polyoxyethylenated sterols;

(3) optionally polyoxyethylenated polyol esters;

(4) natural or synthetic glycolipids; and (5) oxyethylenated polyglycerol stearate.

The amphiphilic ionic lipids used according to the invention for the preparation of the oily core- or aqueous core-containing lipid vesicles are preferably selected from neutralized anionic lipids, amphoteric lipids and the alkylsulphonic derivatives and more particularly from:

the alkali metal salts of dicetyl and dimyristyl phosphate, the alkali metal salts of cholesterol sulphate, the alkali metal salts of cholesterol phosphate, the mono- and disodium acyl glutamates, and in particular the mono- and disodium salts of N-stearoylglutamic acid;

the sodium salts of phosphatidic acid, the alkylsulphonic derivatives of formula:

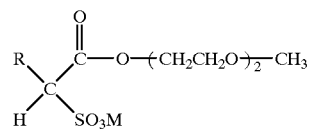

in which formula R represents the radicals $C_{16}H_{33}$ and $C_{18}H_{37}$ taken as a mixture or separately and M is an alkali metal, phosphoaminolipids;

natural phospholipids such as egg or soyabean lecithin, sphingomyelin, phosphatidyiserine, dipalmitoylphosphatidylcholine and hydrogenated lecithins.

The aqueous core-containing vesicles in accordance with the invention advantageously have a mean diameter ranging from 10 to 1000 nm.

The aqueous core-containing vesicles according to the invention are provided in the composition in proportions preferably ranging from 0.5 to 15% by weight relative to the total weight of the composition.

A particularly preferred form of aqueous core-containing vesicles comprises vesicles comprising a lipid membrane obtained from a mixture of polyoxyethylenated soyabean sterols and of hydrogenated lecithin.

The lipophilic surfactants and the hydrophilic surfactants used for the preparation of the oily core-containing vesicles preferably each comprise at least one saturated fatty chain having more than about 12 carbon atoms. Still more preferably, this fatty chain contains from 16 to 22 carbon atoms.

According to another preferred embodiment of the invention, the lipophilic surfactant has an HLB ranging from about 2 to about 5. As is well known, HLB (Hydrophilic-Lipophilic Balance) is understood to mean the equilibrium between the size and the strength of the hydrophilic group and the size and the strength of the lipophilic group of the surfactant.

Examples of such lipophilic surfactants are sucrose distearate, diglyceryl distearate, glyceryl tristearate, decaglyceryl decastearate, diglyceryl monostearate, hexaglyceryl tristearate, decaglyceryl pentastearate, sorbitan monostearate, sorbitan tristearate, diethylene glycol monostearate, glycerol and palmitic and stearic acid esters, polyoxyethylenated monostearate 2 EO (comprising 2 moles of ethylene oxide), glyceryl mono- and dibehenate and penterythritol tetrastearate.

The hydrophilic surfactant preferably has an HLB ranging from about 8 to about 12.

The following compounds may be mentioned as examples of such hydrophilic surfactants: polyoxyethylenated sorbitan monostearate 4 EO, polyoxyethylenated sorbitan tristearate 20 EO, polyoxyethylenated monostearate 8 EO, hexaglyceryl monostearate, polyoxyethylenated monostearate 10 EO, polyoxyethylenated distearate 12 EO and polyoxyethylenated methylglucose distearate 20 EO.

The fatty acid is, according to the invention, preferably selected from the saturated $C_{16}$–$C_{22}$ fatty acids. There may be mentioned, for example, palmitic acid, stearic acid, arachidic acid and behenic acid.

The basic agent contained in the aqueous phase of the dispersion of oily core-containing vesicles, combined with the fatty acid, is selected for example from sodium hydroxide, triethanolamine, lysine or arginine.

Lipid vesicles are more particularly used in the form of an aqueous dispersion of oily globules coated with a layer obtained from sucrose distearate, oxyethylenaled sorbitan monostearate containing 4 moles of ethylene oxide and a disodium salt of acylglutamic acid.

The oily core-containing lipid vesicles as described above preferably have a mean size of less than 500 nanometres and more particularly less than 200 nanometres.

The coated oily globules preferably represent 0.5 to 50% by weight relative to the total weight of the composition.

Another subject of the invention is a cosmetic and/or dermatological composition containing an aqueous dispersion of lipid vesicles, characterized in that it contains at least one acidic compound conferring an acidic pH on the dispersion and at least one cross-linked poly(2-acrylamido-2-methylpropanesulfonic acid) which is at least 90% neutralized.

The compositions in accordance with the invention comprising acidic active agents have a pH preferably less than 5 and more particularly ranging from 2.8 to 4.8.

As organic acidic active agents which can be solubilized in the composition of the invention, there may be mentioned ascorbic acid, kojic acid, citric acid, caffeic acid, salicylic acid and its derivatives (for example 5-n-octanoyl- or 5-decanoylsalicylic acid), α-hydroxy acids such as lactic acid, methyllactic acid, glucuronic acid, glycolic acid, pyruvic acid, 2-hydroxybutanoic acid, 2-hydroxypentanoic acid, 2-hydroxyhexanoic acid, 2-hydroxyheptanoic acid, 2-hydroxyoctanoic acid, 2-hydroxynonanoic acid, 2-hydroxydecanoic acid, 2-hydroxyundecanoic acid, 2-hydroxydodecanoic acid, 2-hydroxytetradecanoic acid, 2-hydroxyhexadecanoic acid, 2-hydroxyoctadecanoic acid, 2-hydroxytetracosanoic acid, 2-hydroxyeicosanoic acid, mandelic acid, beizoic acid, phenyllactic acid, gluconic acid, galacturonic acid, citric acid, aleuritic acid, ribonic acid, tartronic acid, tartaric acid, malic acid, fumaric acid, retinoic acid and its derivatives, 1,4-benzenedi(3-methylidene-10-camphosulphonic) acid, urocanic acid, 2-phenylbenzimidazole-5-sulphonic acid, α-(2-oxo-3-bornylidene)toluene-4-sulphonic acid, 2-hydroxy-4-methoxy-5-sulphonic acid. It is also possible to use all the natural or synthetic compounds containing such acids, such as plant extracts and more especially fruit extracts. It is also possible to solubilize the acidic xanthine derivatives (caffeine, theophylline), β-glycyrrhetinic acid, asiatic acid.

The α-hydroxy acids derived from fruits, such as glycolic, lactic, citric, tartaric, malic or mandelic acids or mixtures thereof, are more particularly used.

The acidic compounds are present in the compositions of the invention in proportions preferably ranging from 0.1 to 10% by weight relative to the total weight of the composition and more preferably from 0.2 to 5% by weight and more particularly from 0.5 to 4% by weight.

The acidic compound may be present in the aqueous phase of the dispersion of aqueous or oily core-containing vesicles or alternatively in the inner aqueous phase of the aqueous core-containing vesicles.

When the composition is in the form of an aqueous dispersion of oily or aqueous core-containing vesicles, the acid compound may be introduced into the external aqueous phase, with stirring, in the dispersion of vesicles which is already formed.

A specific embodiment of the invention is a composition comprising an aqueous dispersion of oily core-containing vesicles mixed with a dispersion of aqueous core-containing vesicles encapsulating the acid compound, the acidic compound is in this case introduced into the dispersion of oily core-containing vesicles which has already formed by means of a dispersion of aqueous core-containing vesicles encapsulating the water-soluble acid compound.

The aqueous phase of the dispersion of the composition according to the invention may also contain a water-immiscible liquid dispersed by the lipid vesicles.

The water-immiscible liquid, which may be present in the form of a dispersion in the aqueous dispersion phase, may be selected in particular from:

animal or vegetable oils consisting of fatty acid and polyol esters, in particular liquid triglycerides, for example sunflower, maize, soyabean, gourd, grapeseed, jojoba, sesame and hazelnut oils, fish oils, glycerol tricaprocaprylate, or vegetable or animal oils of formula $R_8COOR_9$, in which formula $R_8$ represents the residue of a higher fatty acid comprising from 7 to 19 carbon atoms and $R_9$ represents a branched hydrocarbon chain containing from 3 to 20 carbon atoms, for example Purcellin oil;

natural or synthetic essential oils such as, for example, eucalyptus, lavandine lavender, vetiver, Litsea cubeba, lemon, sandalwood, rosemary, camomile, savory, nutmeg, cinnamon, hyssop, caraway, orange, geraniol, cade and bergamot oils;

hydrocarbons such as hexadecane and paraffin oil;

halogenated hydrocarbons, in particular fluorocarbons such as fluoroamines, for example perfluorotributylamine, fluorinated hydrocarbons, for example perfluorodecahydronaphthalene, fluoroesters and fluoroethers;

silicones, for example polysiloxanes, polydimethylsiloxanes and fluorosilcones;

esters of inorganic acid and an alcohol; and ethers and polyethers.

The aqueous dispersion phase may also contain water-soluble cosmetic and/or dermopharmaceutical active agents. The water-immiscible liquid may optionally contain a fat-soluble active agent.

The aqueous dispersion phase may also contain adjuvants having no inherent cosmetic activity or dermopharmaceutical activity, but which are used for formulation of the dispersion in lotion, cream or serum form. These adjuvants are in particular selected from the group consisting of preservatives, colourings, pigments, opacifiers, perfumes, sunscreens and powders for cosmetic use.

The aqueous dispersion phase may contain pigments, nanopigments, coated or uncoated nanotitaniums, soluble colourings. Matting powders may also be added. There may be mentioned, for example, starch powders, nylon powders, silica microspheres, mica platelets coated with silica microspheres.

Another subject of the invention relates to the use of the compositions defined above as base for care or make-up products (tinted cream, foundation) for the face and/or the body.

These products may be provided in the form of dispersions thickened to a greater or lesser degree, gels, creams, milks or serums.

Finally, the invention relates to the use of the composition as defined above in and for the preparation of cosmetic products intended for the treatment of wrinkles and/or fine lines on the skin or of comedones as well as a method for the cosmetic treatment of wrinkles and/or of fine lines on the skin or of comedones, involving applying an effective quantity of the composition of the invention to the skin.

Other characteristics and advantages of the invention will emerge more clearly from the following examples which are given by way of illustration and with no limitation being implied.

PREPARATION EXAMPLE A 2006.2 g of tert-butanol were introduced into a 5 litre round-bottomed flask provided with a stirrer, a reflux condenser, a thermometer and a device for delivering nitrogen and aqueous ammonia, and then 340.0 g of 2-acrylamido-2-methylpropanesulphonic acid were introduced and dispersed in the solution with vigorous stirring. After 30 minutes, aqueous ammonia was added through the top conduit of the round-bottomed flask and the reaction mixture was kept for 30 minutes at room temperature until a pH of the order of 6–6.5 was obtained. 32.0 g of 25% trimethylolpropane triacrylate solution in tert-butanol were then introduced and the mixture was heated to 60° C. while the reaction medium was simultaneously made inert by supplying nitrogen to the round-bottomed flask. Once this temperature was reached, dilauroylperoxide was added. The reaction started immediately, which resulted in a rise in temperature and in precipitation of the polymerizate. 15 minutes after the onset of the polymerization, a nitrogen stream was introduced. 30 minutes after the addition of the initiator, the temperature of the reaction medium reached a maximum of 65–70° C. 30 minutes after having reached this temperature, the medium was heated under reflux and maintained under these conditions for 2 hours. The formation of a thick paste was observed during the reaction. The medium was cooled to room temperature and the product obtained was filtered off. The paste recovered was then dried under vacuum at 60–70° C. for 24 hours. 391 g of cross-linked and neutralized poly(2-acrylamido-2-methylpropanesulphonic acid) having a viscosity, measured with a BROOKFIELD viscometer, rotor 4, at a speed of rotation of 100 revolutions/minute in a solution of water at 2% and at 25° C., ranging from 13,000 cps to 35,000 cps, were obtained. The viscosity of the polymer will be selected and controlled based on conventional means according to the cosmetic application envisaged.

The hydrodynamic radius of the polymer obtained in an aqueous solution, determined by dynamic light scattering, was 440 nm.

EXAMPLE 1

Foundation (Dispersion of Aqueous Core-containing Vesicles, of pH 3.3)

| | |
|---|---|
| Phase $A_1$: | |
| Nonstabilized oxyethylenated soyabean sterols containing 5 EO sold under the name GENEROL 122E5 | 1.6 g |
| Hydrogenated lecithin sold under the name LECINOL S10 | 2.4 g |
| Phase $A_2$: | |
| Sterile demineralized water | 15 g |
| Phase $A_3$: | |
| Sterile demineralized water | 14 g |
| Preservative | 0.2 g |
| Glycerin | 3 g |
| Propylene glycol | 3 g |
| Phase $B_1$: | |
| Palm oil | 6.5 g |
| Nonstabilized deodorized apricot stone oil | 9.5 g |
| Preservatives | 0.19 g |
| Phase $B_2$: | |
| Cyclopentadimethylsiloxane | 10 g |
| Phase $B_3$: | |
| Vitamin E acetate | 0.5 g |
| Sunscreen | 1 g |
| Phase C: | |
| Pigments | 7 g |
| Phase D: | |
| Sterile demineralized water | 1 g |
| Preservative | 0.3 g |
| Phase E: | |
| Sterile demineralized water | 18.84 g |
| Poly(2-acrylamido-2-methylpropanesulphonic acid) AM, cross-linked and neutralized with aqueous ammonia, prepared according to the process of preparation example A | 0.9 g |

-continued

Phase F:

| | |
|---|---|
| Mixture of alpha-hydroxy acids derived from fruit (lactic/glycolic/citric acid 30/15/4) in water (pH = 2) | 1 g |

Phase G:

| | |
|---|---|
| Starch powder | 3 g |
| Sterile demineralized water | qs 100 g |

Procedure

I-PREPARATION OF THE VESICULAR PHASE A:

Preparation of $A_1$:

The water for part $A_1$ was introduced at 85° C. The oxyethylenated soyabean sterols (GENEROL 122 E5) were added, with stirring. A yellow and viscous oil was obtained. The hydrogenated lecithin was added, with stirring, over 15 min. A brittle beige paste was obtained. The temperature was kept at 85° C., with stirring.

Preparation of $A_3$:

The water for $A_3$ was introduced at 85° C.

Propylene glycol, glycerin and the preservative were added, with Moritz stirring at 300 rpm.

Use of the vesicular phase A:

$A_2$ (water) at 85° C. was added to $A_1$ in 3 portions, with stirring, over 15 minutes. The $A_1+A_2$ mixture was allowed to swell for 1 hour.

$A_3$ was introduced at 85° C., with stirring, through the top of the vessel. The medium was stirred for 10 min. It was cooled to 55° C., with stirring.

High-pressure homogenization run

At 55° C., 3 runs were carried out in a high-pressure homogenizer (500 bar).

After the third run, the product was transferred and cooled to 40° C., with stirring.

II-PREPARATION OF $B_1+B_2+B_3$

Palm oil, apricot stone oil and preservative were introduced. The medium was heated to 80° C., with Moritz stirring 500 rpm, until complete homogenization was obtained. The medium was cooled to 65° C. Volatile silicone was introduced. Vitamin E acetate and sunscreen were added, with Moritz stirring 700 rpm. The medium was cooled to 40° C.

III-PREPARATION OF THE VESICULAR DISPERSION+ OILS

Portion B was introduced into portion A. The medium was stirred for 10 min. It was cooled to 25° C., with stirring.

6 runs were carried out in a high-pressure homogenizer (500 bar).

IV-DISPERSION OF THE PIGMENTS

A portion of the product was transferred and the pigments (phase C) were added thereto. The medium was stirred for 1 hour. The dispersion of C was checked under a microscope (there should be no mass of pigments greater than 30 microns).

The remainder of the product was transferred, with stirring. The temperature was kept at 30° C.

V-PREPARATION OF D

The preservative was solubilized in water at room temperature.

VI-PREPARATION OF E

The thickening polymer was dispersed in hot water at a temperature of 80° C. in a deflocculating device.

VII-ADDITION OF PHASES D, E, F, G

D was added and the medium was homogenized, with stirring, for 5 minutes.

E was added and the medium was homogenized for 5 min, with stirring. Good dispersion of the gel was checked under a microscope. The mixture of alpha-hydroxy acids (phase F) was added followed by starch (G), with stirring for 5 min. The medium was cooled to 25° C., with stirring, and then the stirring was stopped. A sample was collected for checking.

The composition obtained was stable at room temperature after five and ialf months of storage. It was also stable after 2 months of storage in an incubator at 45° C.

EXAMPLE 2

TINTED CREAM (Dispersion of Aqueous Core-containing Vesicles)

The composition was prepared according to the same procedure of Examnple 1 and comprises the following ingredients:

| | |
|---|---|
| Oxyethylenated soyabean sterol containing 5 EO sold under the name GENEROL 122 E5 | 1.6 g |
| Hydrogenated lecithin LECINOL S10 | 2.4 g |
| Mixture of natural tocopherols in soyabean oil (50/50) | 0.2 g |
| Mixture of refined maize/rice bran/sesame/wheat germ oils (29/40/20/10) | 5 g |
| Nonstabilized deodorized apricot stone oil | 7 g |
| Propylene glycol | 3 g |
| Sunscreen | 2 g |
| Preservatives | 0.35 g |
| Cyclohexadimethylsiloxane | 10 g |
| Vitamins | 2.8 g |
| Pigments | 5 g |
| Mixture of alpha-hydroxy acids derived from fruit (lactic/glycolic/citric acid 30/15/4) in water | 1 g |
| Poly(2-acrylamido-2-methylpropanesulphonic acid) AM, cross-linked and neutralized with aqueous ammonia, prepared according to the procedure of Preparation Example A | 0.9 g |
| Demineralized water | 59.75 g |

The composition obtained was stable at room temperature after five and half months of storage. It was also stable after 2 months of storage at 45° C.

EXAMPLE 3

Foundation (Dispersion of Oily Centre-containing Vesicles of pH 4.7)

Phase $A_1$:

| | |
|---|---|
| Sucrose distearate | 2.4 g |
| Oxyethylenated sorbitan stearate containing 4 moles of ethylene oxide | 1.6 g |
| Disodium salt of N-stearoylglutamic acid | 1.2 g |
| Mixtures of sunflower, rose, muscat and blackcurrant seed oils (31/60/5.95/3) | 5 g |
| Hydrogenated isoparaffin | 9 g |
| Polydimethylsiloxane of viscosity 5 cst | 9 g |
| Vitamin E | 0.09 g |
| Sunscreen | 1 g |

Phase $A_2$:

| | |
|---|---|
| Sterile demineralized water | 35 g |
| EDTA | 0.05 g |
| Glycerin | 4 g |

Phase $B_1$:

| | |
|---|---|
| Sterile demineralized water | 11.85 g |
| Sodium and magnesium silicate | 0.3 g |

-continued

| Phase B₂: | |
|---|---|
| Pigments | 9 g |
| Phase C: | |
| Sterile demineralized water | 1 g |
| Preservative | 0.3 g |
| Phase D: | |
| Polyethylene glycol (80 EO) | 5 g |
| Phase E: | |
| Matting powder | 2 g |
| Phase F: | |
| Poly(2-acrylamido-2-methylpropanesulphonic acid) | 0.4 g |

AM, cross-linked and neutralized with aqueous ammonia, prepared according to the procedure of Preparation Example A

| Phase G: | |
|---|---|
| Lactic acid in water | 1 g |
| Sterile demineralized water | qs 100 g |

Procedure

I-MANUFACTURE OF THE VESICULAR PHASE A

Phase $A_1$ was melted at 85–90° C.

It was homogenized.

In parallel, phase $A_2$ was prepared (dissolution of EDTA) and it was brought to 60° C.

Phase $A_2$ was poured over phase $A_1$ rapidly and with vigorous stirring. The medium was homogenized at 60° C. for 10 min. The whole mixture was subjected to a high-pressure homogenization run, at 500 bar. A minimum of 2 runs were necessary. A diameter of 200 nm should be obtained for a polydispersity of less than 1.

The mixture was cooled to 30° C. and deaerated.

II-PREPARATION OF THE PIGMENT DISPERSION

In parallel, magnesium and sodium silicate gel was prepared using a homogenizer.

The pigments (phase $B_2$) were dispersed in the gel. The medium was cooled to 35° C. over 15 min. Phase C (preservative) was introduced.

The dispersion was continued over one and half hour in total.

III-DISPERSION OF THE VESICULAR DISPERSION IN THE PIGMENT DISPERSION

The vesicular phase at 30° C. was introduced in several stages into the pigment dispersion, with turbine and high-speed blade stirring.

The medium was mixed in a turbine mixer for 1 hour. Phase D was added by gravity. The medium was homogenized for 5 minutes.

Phase E (powder) was added and the medium was homogenized for 2 minutes. Phase F (gelling agent) was added and the medium was homogenized for 10 minutes. It was subjected to maximum deaeration.

IV-INTRODUCTION OF THE ALPHA-HYDROXY ACIDS

Phase G was added to the formula thus obtained in gelled form, with high-speed blade stirring. The medium was homogenized for 5 minutes.

The composition obtained was stable at room temperature.

EXAMPLE 4

Foundation (Dispersion of Oily Centre-containing Vesicles)

The composition was prepared according to the same procedure of Example 3 and comprises the following ingredients:

| | |
|---|---|
| Sucrose distearate | 2.4 g |
| Oxyethylenated sorbitan stearate containing 4 moles of ethylene oxide | 1.6 g |
| Disodium salt of N-stearoylglutamic acid | 1.2 g |
| Mixture of refined maize/rice bran/sesame/ wheat germ oils (29/40/20/10) | 5 g |
| Deodorized apricot stone oil | 2 g |
| Nonstabilized sweet almond oil | 2 g |
| Hydrogenated isoparaffin | 9 g |
| Polydimethylsiloxane of viscosity 5 cst | 9 g |
| Cyclohexadimethylsiloxane of viscosity 8 cst | 2 g |
| Vitamin E | 0.5 g |
| Sunscreen | 1 g |
| EDTA | 0.02 g |
| Glycerine | 5 g |
| Sodium and magnesium silicate | 0.3 g |
| Pigments | 7 g |
| Sterile demineralized water | 1 g |
| Preservatives | 0.75 g |
| Starch powder | 2 g |
| Poly(2-acrylamido-2-methylpropanesulphonic acid) AM, cross-linked and neutralized with aqueous ammonia, prepared according to the process of Preparation Example A | 0.25 g |
| Sterile demineralized water | 54.18 g |

EXAMPLE 5

Foundation (Dispersion of Oily Core-containing Vesicles and of Aqueous Core-containing Vesicles Encapsulating the α-hydroxy Acids pH 4.7)

| Phase $A_1$: | |
|---|---|
| Sucrose distearate | 1.8 g |
| Oxyethylenated sorbitan stearate containing 4 moles of ethylene oxide | 1.6 g |
| Disodium salt of N-stearoylglutamic acid | 0.9 g |
| Stabilized mixture of sunflower, rose, nutmeg and blackcurrant seed oils (31/60/5.95/3) | 3.70 g |
| Hydrogenated isoparaffin (8 EO) | 6.70 g |
| Polydimethylsiloxane 5 cst | 6.70 g |
| Vitamin E | 0.06 g |
| Sunscreen | 0.70 g |
| Phase $A_2$: | |
| Sterile demineralized water | 26.12 g |
| EDTA, disodium salt | 0.03 g |
| Glycerin | 2.98 g |
| Phase $B_1$: | |
| Sterile demineralized water | 7.24 g |
| Sodium and magnesium silicate | 0.22 g |
| Phase $B_2$: | |
| Pigments | 6.72 g |
| Phase C: | |
| Demineralized water | 0.74 g |
| Preservative | 0.22 g |
| Phase D: | |
| Polyethylene glycol (8 EO) | 3.73 g |

-continued

| Phase E: | |
|---|---|
| Matting powder | 1.49 g |
| Phase F: | |
| Poly(2-acrylamido-2-methylpropanesulphonic acid) | 0.3 g |

AM, cross-linked and neutralized with aqueous ammonia, prepared according to the procedure of Preparation Example A

| Phase $G_1$: | |
|---|---|
| GENEROL 122 E5 | 1.20 g |
| LECINOL S10 | 1.8 g |
| Sterile demineralized water | 11.20 g |
| Phase $G_2$: | |
| Sterile demineralized water | 10.45 g |
| Preservative | 0.07 g |
| Propylene glycol | 2.24 g |
| Mixture of lactic/glycolic/citric acids (30/15/4) in water pH = 2 | 0.75 g |
| Sterile demineralized water | qs 100 g |

Procedure

The dispersion of oily core-containing vesicles was prepared from phases $A_1$, $A_2$, $B_1$, $B_2$, C, D, E and F according to the same steps of the procedure of Example 3 preceding the introduction of the α-hydroxy acids.

An aqueous centre-containing vesicular phase (phase $G_1$) was prepared to which phase $G_2$ containing the α-hydroxy acids was added during the second hydration.

This vesicular phase was then considered as being active and was added, with high-speed blade stirring to the dispersion of oily core-containing vesicles already formed.

The composition obtained was stable at room temperature.

EXAMPLE 6
(Comparative)

The inventors prepared the following three compositions:

| Composition A: (invention) | |
|---|---|
| Phase $A_1$: | |
| Nonstabilized oxyethylenated soyabean sterols containing 5 EO sold under the name GENEROL 122E5 | 1.6 g |
| Hydrogenated lecithin sold under the name LECINOL S10 | 2.4 g |
| Phase $A_2$: | |
| Sterile demineralized water | 15 g |
| Phase $A_3$: | |
| Sterile demineralized water | 14 g |
| Preservative | 0.2 g |
| Glycerin | 3 g |
| Propylene glycol | 3 g |
| Phase $B_1$: | |
| Nonstabilized deodorized apricot stone oil | 12 g |
| Preservatives | 0.15 g |

-continued

| Composition A: (invention) | |
|---|---|
| Phase $B_2$: | |
| Cyclohexadimethylsiloxane | 12 g |
| Phase $B_3$: | |
| Sunscreen | 2 g |
| Phase C: | |
| Sterile demineralized water | 1 g |
| Preservative | 0.3 g |
| Phase D: | |
| Sterile demineralized water | 35.28 g |
| Poly(2-acrylamido-2-methylpropanesulphonic acid) | 0.72 g |

AM, Cross-linked and Neutralized with Aqueous Aammonia, Prepared According to the Procedure of Preparation Example A

| Phase E: | |
|---|---|
| Sterile demineralized water | qs 100 g |
| Composition B: (Comparative) | |
| Phase $A_1$: | |
| Nonstabilized oxyethylenated soyabean sterols containing 5 EO sold under the name GENEROL 122E5 | 1.6 g |
| Hydrogenated lecithin sold under the name LECINOL S10 | 2.4 g |
| Phase $A_2$: | |
| Sterile demineralized water | 15 g |
| Phase $A_3$: | |
| Sterile demineralized water | 14 g |
| Preservative | 0.2 g |
| Glycerin | 3 g |
| Propylene glycol | 3 g |
| Phase $B_1$: | |
| Nonstabilized deodorized apricot stone oil | 12 g |
| Preservatives | 0.15 g |
| Phase $B_2$: | |
| Cyclohexadimethylsiloxane | 12 g |
| Phase $B_3$: | |
| Sunscreen | 2 g |
| Phase C: | |
| Sterile demineralized water | 1 g |
| Preservative | 0.3 g |
| Phase D: | |
| Mixture of polyacrylamide, isoparaffin, oxyethylenated lauryl alcohol in water (40/34.5/5.5/20) | 1.8 g that is to say 0.72 g AM |
| Phase E: | |
| Sterile demineralized water | qs 100 g |
| Composition C: (Comparative) | |
| Phase $A_1$: | |
| Nonstabilized oxyethylenated soyabean sterols containing 5 EO sold under the name GENEROL 122E5 | 1.6 g |
| Hydrogenated lecithin sold under the name LECINOL S10 | 2.4 g |
| Phase $A_2$: | |
| Sterile demineralized water | 15 g |

-continued

Phase A₃:

| | |
|---|---|
| Sterile demineralized water | 14 g |
| Preservative | 0.2 g |
| Glycerin | 3 g |
| Propylene glycol | 3 g |

Phase B₁:

| | |
|---|---|
| Nonstabilized deodorized apricot stone oil | 12 g |
| Preservatives | 0.15 g |

Phase B₂:

| | |
|---|---|
| Cyclohexadimethylsiloxane | 12 g |

Phase B₃:

| | |
|---|---|
| Sunscreen | 2 g |

Phase C:

| | |
|---|---|
| Sterile demineralized water | 1 g |
| Preservative | 0.3 g |

Procedure

I-PREPARATION OF THE VESICULAR PHASE A:

Preparation of A₁:

The water of part A₁ was introduced at 85° C. The oxyethylenated soyabean sterols (GENEROL 122 E5) were added, with stirring. A yellow and viscous oil was obtained. The hydrogenated lecithin was added, with stirring, over 15 min. A brittle beige paste was obtained. The temperature was kept at 85° C., with stirring.

Preparation of A₃;

The water for A₃ was introduced at 85° C.

Propylene glycol, glycerin and the preservative were added, with Moritz stirring at 300 rpm.

Use of the vesicular phase A:

A₂ (water) at 85° C. was added to A₁ in 3 portions, with stirring, over 15 minutes.

The A₁+A₂ mixture was allowed to swell for 1 hour.

A₃ was introduced at 85° C., with stirring, through the top of the vessel. The medium was stirred for 10 min. It was cooled to 55° C., with stirring.

High-pressure homogenization run

At 55° C., 3 runs are carried out in a high-pressure homogenizer (500 bar).

After the third run, the product is transferred and cooled to 40° C., with stirring.

II-PREPARATION OF B₁+B₂+B₃

Apricot stone oil and preservative were introduced. The medium was heated to 80° C., with Moritz stirring 500 rpm, until complete homogenization was obtained. The medium was cooled to 65° C. Volatile silicone was introduced. Sunscreen was added, with Moritz stirring 700 rpm. The medium was cooled to 40° C.

III-PREPARATION OF THE VESICULAR DISPERSION+ OILS

Portion B was introduced into portion A. The medium was stirred for 10 min. It was cooled to 25° C., with stirring.

6 runs were carried out in the high-pressure homogenizer (500 bar).

IV-PREPARATION OF C

The preservative was solubilized in water at room temperature.

V-PREPARATION OF D IN COMPOSITION A ACCORDING TO THE INVENTION

The thickening polymer was dispersed in hot water at a temperature of 80° C. using a deflocculating device.

VI-ADDITION OF PHASES D, E

D was added and the medium was homogenized, with stirring, for 5 minutes. Good dispersion of the gel was checked under a microscope.

E was added and the medium was homogenized for 5 min, with stirring. A sample was collected for checking.

These three compositions were stored for 2 months at 45° C. For each of these compositions, a sample was frozen at −200° C. in pasty nitrogen and then each of them was freeze-fractured with the aid of a freeze-fracturing device of the REICHERT-JUNG type at −150° C. under vacuum. After metallizing with platinum and with carbon arid mounting the imprints on nickel grids, the samples were observed under a PHILIPS CM120-type transmission electron microscope at magnifications ranging from 8000 to 75,000.

The results observed are assembled in the table below.

| Composition | Mean diameter of the particles observed in nm |
|---|---|
| Composition A | 540 ± 670 |
| Composition B | 1580 ± 500 |
| Composition C | 2000 ± 660 |

It is evident from these results that the dispersion obtained according to the invention is finer than those obtained in the prior art compositions.

We claim:

1. A cosmetic or dermatological composition comprising an aqueous dispersion of lipid vesicles and at least one cross-linked poly(2-acrylamido-2-methylpropanesulphonic acid), wherein said at least one cross-linked poly(2-acrylamido-2-methylpropanesulphonic acid) is at least 90% neutralized.

2. A cosmetic or dermatological composition according to claim 1, wherein said at least one cross-linked poly(2-acrylamido-2-methylpropanesulphonic acid) is water-soluble or capable of swelling in water.

3. A cosmetic or dermatological composition according to claim 2, wherein said at least one cross-linked poly(2-acrylamido-2-methylpropanesulphonic acid) comprises, distributed in a random manner:

a) from 90 to 99.9% by weight of units of formula (1):

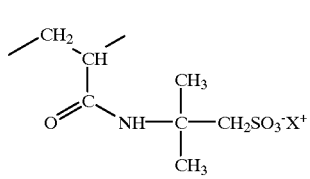

(1)

in which:

X⁺ denotes at least one cation, wherein no more than 10 mol % of the cations X⁺ are protons H⁺;

b) from 0.01 to 10% by weight of cross-linking units obtained from at least one monomer having at least two olefinic double bonds; wherein said percentages by weight are relative to the total weight of said polymer.

4. A cosmetic or dermatological composition according to claim 3, wherein said at least one cross-linked poly(2-acrylamido-2-methylpropanesulphonic acid) comprises a quantity of units of formula (1) sufficient to obtain, in a solution of water, a hydrodynamic volume of said at least one cross-linked poly(2-acrylamido-2-methylpropanesulphonic acid) having a radius ranging from 10 to 500 nm and having homogeneous and unimodal distribution.

5. A cosmetic or dermatological composition according to claim 3, wherein said at least one cross-linked poly(2-acrylamido-2-methylpropanesulphonic acid) comprises from 98 to 99.5% by weight of units of formula (1) and from 0.2 to 2% by weight of cross-linking units (b).

6. A cosmetic or dermatological composition according to claim 3, wherein said at least one cation $X^+$ is $NH_4^+$.

7. A cosmetic or dermatological composition according to claim 3, wherein said at least one cation $X^+$ is selected from protons, alkali metal cations, and ammonium ions.

8. A cosmetic or dermatological composition according to claim 3, wherein from 90 to 100 mol % of said at least one cation are $NH_4^+$ cations and up to 10 mol % are protons $H^+$.

9. A cosmetic or dermatological composition according to claim 3, wherein said cross-linking units (b) are selected from dipropylene glycol diallyl ether, polyglycol diallyl ethers, triethylene glycol divinyl ether, hydroquinone diallyl ether, tetraallyl oxethanoyl and other polyfunctional allyl and vinyl ether alcohols, tetraethylene glycol diacrylate, triallylamine, trimethylolpropane diallyl ether, methylenebisacrylamide and divinylbenzene.

10. A cosmetic or dermatological composition according to claim, 3, wherein said cross-linking units (b) correspond to formula (2):

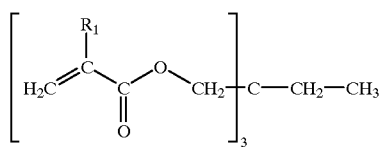

in which:

$R_1$ denotes a hydrogen atom or a $C_1$–$C_4$ alkyl.

11. A cosmetic or dermatological composition according to claim 10, wherein $R_1$ denotes methyl.

12. A cosmetic or dermatological composition according to claim 1, wherein said at least one poly(2-acrylamido-2-methylpropanesulphonic acid) is cross-linked with trimethylolpropane triacrylate.

13. A cosmetic or dermatological composition according to claim 1, wherein said at least one cross-linked poly(2-acrylamido-2-methylpropanesulphonic acid) has a viscosity, measured in a BROOKFIELD viscometer, rotor 4, at a speed of rotation of 100 revolutions/minute, in a solution of water at 2% and at 25° C., of at least 1000 cps.

14. A cosmetic or dermatological composition according claim 13, wherein said viscosity ranges from 5000 to 40,000 cps.

15. A cosmetic or dermatological composition according claim 14, wherein said viscosity ranges from 6500 to 35,000 cps.

16. A cosmetic or dermatological composition according to claim 1, wherein said at least one cross-linked poly(2-acrylamido-2-methylpropanesulphonic acid) is present in an amount ranging from 0.01 to 20% by weight relative to the total weight of said composition.

17. A cosmetic or dermatological composition according to claim 16, wherein said at least one cross-linked poly(2-acrylamido-2-methylpropanesulphonic acid) is present in an amount ranging from 0.1 to 10% by weight relative to the total weight of said composition.

18. A cosmetic or dermatological composition according to claim 1, wherein said composition is an oil-in-water dispersion wherein said lipid vesicles serve as an agent for dispersing oil in the aqueous continous phase.

19. A cosmetic or dermatological composition according to claim 1, wherein said lipid vesicles encapsulate an oily core or an aqueous core.

20. A cosmetic or dermatological composition according to claim 19, wherein said aqueous core lipid vesicles comprise a lipid membrane obtained from at least one lipid selected from nonionic amphiphilic lipids and ionic amphiphilic lipids.

21. A cosmetic or dermatological composition according to claim 19, wherein said oily core lipid vesicles are oily globules in aqueous dispersion, coated with a monolamellar or oligolamellar layer obtained from at least one lipophilic surfactant, one hydrophilic surfactant and either an ionic amphiphilic lipid or a fatty acid combined with a basic agent dissolved in the aqueous phase of said aqueous dispersion.

22. A cosmetic or dermatological composition according to claim 20, wherein said aqueous core lipid vesicles comprise a lipid membrane obtained from oxyethylenated soyabean sterols and hydrogenated lecithin.

23. A cosmetic or dermatological composition according to claim 21, wherein said oily core lipid vesicles are in the form of an aqueous dispersion of oily globules coated with a layer obtained from sucrose distearate, oxyethylenated sorbitan monostearate containing 4 moles of ethylene oxide and a disodium salt of acylglutamic acid.

24. A cosmetic or dermatological composition according to claim 19, wherein said aqueous core lipid vesicles have a mean diameter ranging from 10 to 1000 nm.

25. A cosmetic or dermatological composition according to claim 19, wherein said oily core lipid vesicles have a mean size less than 500 nm.

26. A cosmetic or dermatological composition according to claim 25, wherein said oily core lipid vesicles have a mean size less than 200 nm.

27. A cosmetic or dermatological composition according to claim 19, wherein said aqueous core lipid vesicles are present in an amount ranging from 0.5 to 15% by weight relative to the total weight of said composition.

28. A cosmetic or dermatological composition according to claim 19, wherein said oily core lipid vesicles are present in an amount ranging from 0.5 to 50% by weight relative to the total weight of said composition.

29. A cosmetic or dermatological composition according to claim 1, wherein said composition further comprises at least one cosmetically or dermatologically active acidic compound.

30. A cosmetic or dermatological composition according to claim 29, wherein said at least one active acidic compound is present in the external aqueous phase of said dispersion.

31. A cosmetic or dermatological composition according to claim 29, wherein said at least one active acidic compound is encapsulated in the internal aqueous phase of the aqueous core lipid vesicles.

32. A cosmetic or dermatological composition according to claim 29, wherein said composition comprises a dispersion of oily core lipid vesicles mixed with a dispersion of aqueous core lipid vesicles encapsulating said at least one active acidic compound.

33. A cosmetic or dermatological composition according to claim 29, wherein said composition has a pH less than 5.

34. A cosmetic or dermatological composition according to claim 33, wherein said composition has a pH ranging from 2.8 to 4.8.

35. A cosmetic or dermatological composition according to claim 29, wherein said at least one active acidic compound is present in an amount ranging from 0.1 to 10% by weight relative to the total weight of said composition.

36. A cosmetic or dermatological composition according to claim 35, wherein said at least one active acidic compound is present in an amount ranging from 0.2 to 5% by weight relative to the total weight of said composition.

37. A cosmetic or dermatological composition according to claim 36, wherein said at least one active acidic compound is present in an amount ranging from 0.5 to 4% by weight relative to the total weight of said composition.

38. A cosmetic or dermatological composition according to claim 29, wherein said at least one active acidic compound is selected from: ascorbic acid, kojic acid, citric acid, caffeine acid, salicylic acid and its derivatives, lactic acid, methyllactic acid, glucuronic acid, glycolic acid, pyruvic acid, 2-hydroxybutanoic acid, 2-hydroxypentanoic acid, 2-hydroxyhexanoic acid, 2-hydroxyheptanoic acid, 2-hydroxyoctanoic acid, 2-hydroxynonanoic acid, 2-hydroxydecanoic acid, 2-hydroxyundecanoic acid, 2-hydroxydodecanoic acid, 2-hydroxytetradecanoic acid, 2-hydroxyhexadecanoic acid, 2-hydroxyoctadecanoic acid, 2-hydroxytetracosanoic acid, 2-hydroxyeicosanoic acid, mandelic acid, benzoic acid, phenyllactic acid, glucoric acid, galacturonic acid, aleuritic acid, ribonic acid, tartronic acid, tartaric acid, malic acid, fumaric acid, retinoic acid and its derivatives, 1,4-benzenedi(3-methylidene-10-camphosulphonic) acid, urocanic acid, 2-phenylbenzimidazole-5-sulphonic acid, α-(2-oxo-3-bornylidene)toluene-4-sulphonic acid, 2-hydroxy-4-methoxy-5-sulphonic acid, acidic xanthine derivatives, β-glycyrrhetinic acid, and asiatic acid.

39. A cosmetic or dermatological composition according to claim 38, wherein said acidic xanthine derivatives are selected from caffeine and theophylline.

40. A cosmetic or dermatological composition according to claim 38, wherein at least one active acidic compound is selected from the α-hydroxy acids derived from fruit.

41. A cosmetic or dermatological composition according to claim 40, wherein said at least one active acidic compound is selected from glycolic, lactic, citric, tartaric, malic and mandelic acids.

42. A cosmetic or dermatological composition according to claim 1, wherein said dispersion further comprises at least one water-immiscible liquid dispersed by said lipid vesicles.

43. A cosmetic or dermatological composition according to claim 1, wherein said dispersion further comprises at least one water-soluble cosmetic or dermopharmaceutical active agent.

44. A cosmetic or dermatological composition according to claim 42, wherein said at least one water-immiscible liquid comprises at least one fat-soluble active agent.

45. A method of including a cosmetic or dermatological composition according to claim 1 as a base for a care or make-up product for the body or the face comprising the step of adding said composition to said product.

46. A method according to claim 45, wherein said product is to a form selected from dispersions, gels, creams, milks and serums.

47. A method of preparing a cosmetic product for the treatment of wrinkles or fine lines on the skin or treatment of comedones caused by acne comprising adding to said product a composition according to claim 1.

48. A method for cosmetically treating fine lines or wrinkles on the skin or cosmetically treating comedones caused by acne, comprising applying an effective amount of at least one composition according to claim 1 to said lines, wrinkles or comedones.

49. A cosmetic or dermatological composition according to claim 1, wherein said at least one cross-linked poly (2-acrylamido-2-methylpropane-sulphonic acid) is a homopolymer.

* * * * *